United States Patent
Hong

(10) Patent No.: US 9,539,183 B2
(45) Date of Patent: Jan. 10, 2017

(54) HAIR DYEING METHOD AND HAIR THUS MANUFACTURED

(71) Applicant: HIMO Inc., Seoul (KR)

(72) Inventor: In Pyo Hong, Seoul (KR)

(73) Assignee: HIMO INC., Seoul (KR)

( * ) Notice: Subject to any disclaimer, the term of this patent is extended or adjusted under 35 U.S.C. 154(b) by 0 days.

(21) Appl. No.: 14/850,867

(22) Filed: Sep. 10, 2015

(65) Prior Publication Data

US 2016/0074680 A1    Mar. 17, 2016

(30) Foreign Application Priority Data

Sep. 12, 2014   (KR) ........................ 10-2014-0120884

(51) Int. Cl.
*A61Q 5/10*     (2006.01)
*A61K 8/02*     (2006.01)
*A45D 7/00*     (2006.01)

(52) U.S. Cl.
CPC . *A61K 8/02* (2013.01); *A61Q 5/10* (2013.01); *A45D 2007/001* (2013.01); *A61K 2800/884* (2013.01)

(58) Field of Classification Search
CPC ...... A61Q 5/10; A61K 8/02; A61K 2800/884; A45D 2007/001
See application file for complete search history.

(56) References Cited

U.S. PATENT DOCUMENTS

| | | | |
|---|---|---|---|
| 4,483,354 A | 11/1984 | Marcotte | |
| 5,042,511 A * | 8/1991 | Haddad | A45D 19/18 132/208 |

(Continued)

FOREIGN PATENT DOCUMENTS

| | | | |
|---|---|---|---|
| JP | 3087222 U * | 7/2002 | ............. A45D 44/00 |
| JP | 2002226345 | 8/2002 | |

OTHER PUBLICATIONS

Korean Office Action for corresponding Korean Application No. 10-2014-0120884 filed Sep. 12, 2014.

(Continued)

*Primary Examiner* — Eisa Elhilo
(74) *Attorney, Agent, or Firm* — Wegman, Hessler & Vanderburg

(57) ABSTRACT

Provided are a hair dyeing method which causes a particular portion of hair to attain a different color than the overall color, and hair which is thus manufactured. The method includes steps of (a) applying a first dye to a plurality of hairs, (b) dividing the plurality of hairs, to which the first dye is applied, into specific units of hair, (c) marking a section in the specific unit of hair which will not be dyed, (d) tying the marked section in the specific unit of hair, (e) injecting water into a dyeing apparatus which is to be used in applying a second dye, (f) heating the water which is injected into the dyeing apparatus, (g) injecting a chemical and a dye into the water which is injected into the dyeing apparatus and heated, (h) introducing the specific unit of hair to be mixed with the water which is injected into the dyeing apparatus, (i) gradually raising a temperature of the water which is injected into the dyeing apparatus, (j) when the temperature of the water which is injected into the dyeing apparatus rises to a certain temperature, maintaining the temperature of the water for a certain duration of time, (k) verifying the color of the specific unit of hair, and repeating the step (g) when the color of the specific unit of hair is not a designated color, and (l) when the color of the specific unit of hair is the designated color, stopping the heating of the water which is injected into the dyeing apparatus, and draining the water from the dyeing apparatus.

11 Claims, 3 Drawing Sheets

(56) References Cited

U.S. PATENT DOCUMENTS

2002/0069890 A1 6/2002 Schweickert et al.
2007/0009312 A1* 1/2007 Burghaus ............... A45D 19/02
　　　　　　　　　　　　　　　　　　　　　401/35

OTHER PUBLICATIONS

Notice of Allowance for Korean patent application No. 2014-0120884 dated May 17, 2016.

* cited by examiner

HAIR DYEING METHOD AND HAIR THUS MANUFACTURED

CROSS-REFERENCE TO RELATED APPLICATIONS

This application claims the priority of Korean Patent Application No. 10-2014-0120884 filed on Sep. 12, 2014 with the Korean Intellectual Property Office, the disclosure of which is incorporated herein by reference in its entirety.

TECHNICAL FIELD

The present disclosure relates to a hair dyeing method and hair which is thus manufactured, and more particularly, to a hair dyeing method which causes a particular portion of hair to attain a different color than the overall color, and hair which is thus manufactured.

BACKGROUND

Typically, a human hair is extremely thin, having an average diameter of about 0.05 to about 0.08 mm. For this reason, hair material which is generally used in wigs or materials for increasing hair, or in hair extensions for accessories, is similar to human hair in also being thin.

In addition to natural hair from humans, synthetic hair, which is obtained through fabricating synthetic resin fibers such as nylon, modacrylic, and polyester, is also generally known as hair material.

When dyeing such hair materials, there is difficulty involved in coloring a thin hair material having a diameter of about 0.05 to about 0.08 mm such that a desired appearance is obtained, and in realizing a color and/or color tone which is in accordance with the preferences of individuals. Such hair coloring materials are absolutely required to not be easily discolored or to easily lose color, even when exposed to sunlight or washed, and are also required to have a minimum level of rigidity.

Difficulty is also faced when coloring a portion of a single strand of hair material with a different color or color tone than the remaining portion.

An excessively complex process is required to divide a single strand of hair into two or more parts and color each part with a different color.

In Japanese Patent Application Laid-open Publication No. 174683/89, a related art for coloring hair is disclosed.

Such related art for coloring hair requires particular care to prevent a remaining portion of hair material which is not to be colored, from being inadvertently dipped in dyeing solution. In this method, for example, when about 5 cm of a middle portion of hair material needs to be colored, only exactly this middle portion may be dipped in dyeing solution for a certain period of time.

Since accurately maintaining the hair material is required to prevent inadvertently dipping the portion of hair material which should not be dyed into a dyeing solution, there is a limitation in that control for accurately coloring a designated portion of the hair material is difficult.

When various types or a plurality of colors or color tones must be separately colored on hair material, the portion of hair which is designated to be colored is required to be dipped in a dye container each time that coloring is performed, and thus the number of steps is increased.

Thus, such a dipping method is limited in being difficult to apply in cases which require partial coloring, or in cases which require a single strand of hair to be colored with two or more colors or color tones.

SUMMARY

The present disclosure was conceived to overcome such limitations as above, and it is an objective thereof to provide a hair dyeing method in which the application of color is only excluded in a particular portion, and to provide hair which is thus manufactured.

A hair dyeing method for achieving such objectives as above includes steps of (a) applying a first dye to a plurality of hairs; (b) dividing the plurality of hairs, to which the first dye is applied, into specific units of hair; (c) marking a section in the specific unit of hair which will not be dyed; (d) tying the marked section in the specific unit of hair; (e) injecting water into a dyeing apparatus which is to be used in applying a second dye; (f) heating the water which is injected into the dyeing apparatus; (g) injecting a chemical and a dye into the water which is injected into the dyeing apparatus and heated; (h) introducing the specific unit of hair to be mixed with the water which is injected into the dyeing apparatus; (i) gradually raising a temperature of the water which is injected into the dyeing apparatus; (j) when the temperature of the water which is injected into the dyeing apparatus rises to a certain temperature, maintaining the temperature of the water for a certain duration of time; (k) verifying the color of the specific unit of hair, and repeating the step (g) when the color of the specific unit of hair is not a designated color; (l) when the color of the specific unit of hair is the designated color, stopping the heating of the water which is injected into the dyeing apparatus, and draining the water from the dyeing apparatus.

In the step (b) the plurality of hairs may be divided into the specific unit of about 2 to about 3 grams.

In the step (f) a steam unit which is installed in the dyeing apparatus may be used to heat the water.

The step (g) may further include the steps of (g)-1 measuring and preparing the chemical; (g)-2 when the water temperature of the water which is injected into the dyeing apparatus reaches 60° C., injecting the chemical into the water which is injected into the dyeing apparatus; and (g)-3 measuring and dissolving the calculated dye in water, and then injecting the dye into the water which is injected into the dyeing apparatus.

In the step (h) the water which is injected into the dyeing apparatus may be stirred such that the specific unit of hair and the water which is injected into the dyeing apparatus are mixed.

In the step (i) the temperature of the water which is injected into the dyeing apparatus may be raised up to about 100° C.

In the step (l) a mesh may be used to collect hair which is discharged along with the water which is drained from the dyeing apparatus.

The step of (m) washing with water the specific unit of hair for which dyeing is completed may be further included.

The step of (n) dissolving a softening agent in 50° C. water to soften the specific unit of hair which is washed with water may be further included.

The step of (o) drying the specific unit of hair which is softened may be further included.

A hair which was manufactured through a hair dyeing method according to the present disclosure such as above to achieve an objective such as above may include a colored part which is colored by a chemical and dye; and an uncolored part which is not colored by the chemical and dye.

A knotting material which is tied to the uncolored part may be further included.

DETAILED DESCRIPTION

Hereinafter, with reference to accompanying figures, the composition and effects of an exemplary embodiment of the present disclosure are described in detail, as follows. The below embodiments may be modified into various forms, and the scope of the present disclosure is not limited to the below embodiments.

Figure 1:
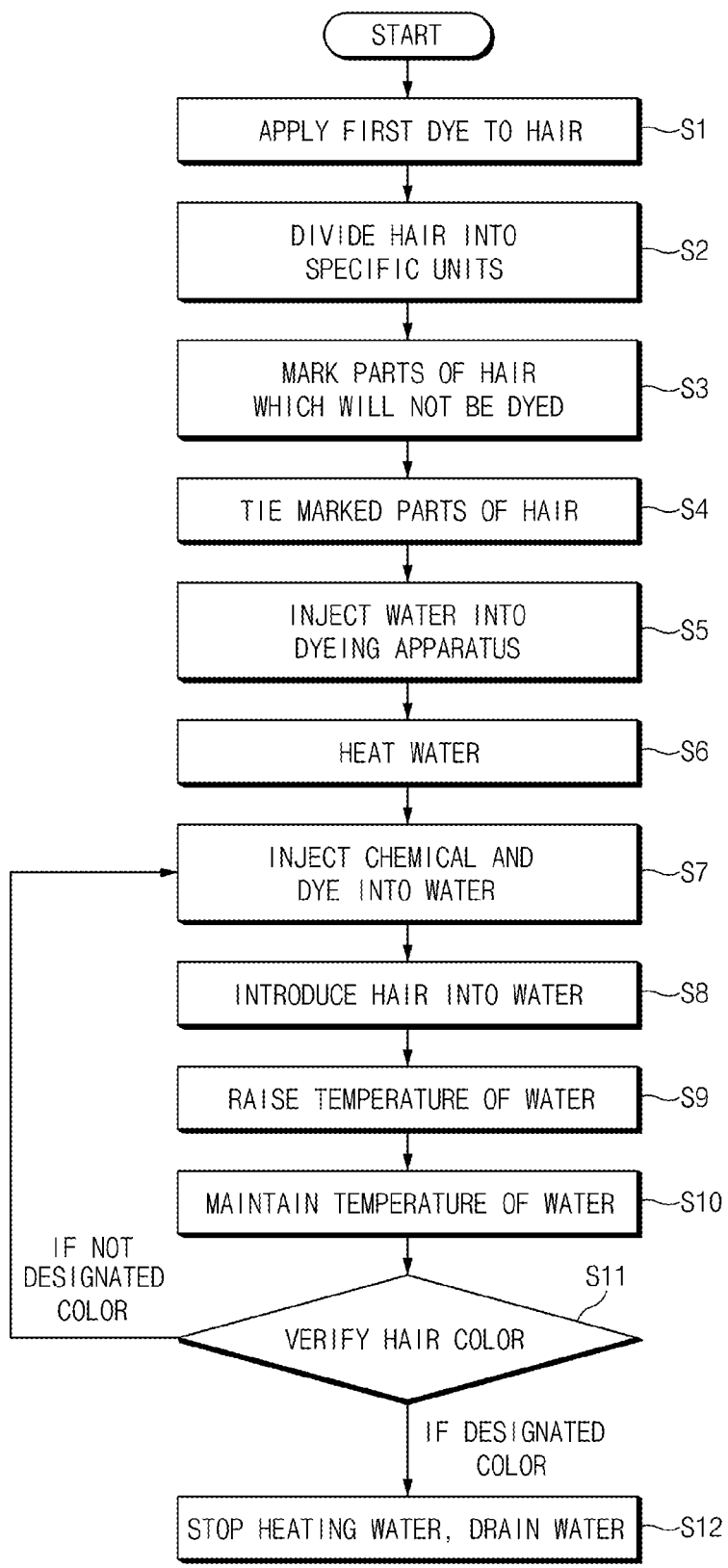
FIG. 1 is a flow chart in which a hair dyeing method according to an embodiment of the present disclosure is illustrated sequentially.

FIG. 1 is a flow chart sequentially illustrating a hair dyeing method according to an embodiment of the present disclosure.

Referring to FIG. 1, a hair dyeing method according to an exemplary embodiment of the present disclosure includes a first step S1 in which a basic first dye is applied to a plurality of hairs.

The plurality of hairs may be one or more human or synthetic (polyester) hairs.

A hair dyeing method according to an exemplary embodiment of the present disclosure includes a second step S2 in which the plurality of hairs are divided into specific units of hair.

Here, the specific unit may be the unit of about 2 to about 3 grams, but may be suitably modified in accordance with the situation.

A hair dyeing method according to an exemplary embodiment of the present disclosure includes a third step S3 in which an uncolored part 5 in the hair which was divided into the specific unit in the second step and which will not be dyed is measured, and the measured uncolored part 5 is marked by being tied into equal lengths by using a thread, etc.

A hair dyeing method according to an exemplary embodiment of the present disclosure includes a fourth step S4 in which a part in the hair 1 which was marked is tied by using a tool.

The tool may include a knotting material 7 such as a string tie, a string band, and so on.

A hair dyeing method according to an exemplary embodiment of the present disclosure includes a fifth step S5 in which preparation for a second dye is completed, a dyeing apparatus to be used in the second dye is selected, and a required amount of water is injected into the dyeing apparatus.

A hair dyeing method according to an exemplary embodiment of the present disclosure includes a sixth step S6 in which a steam valve which is installed in the dyeing apparatus is opened to heat water which was injected into the dyeing apparatus.

A hair dyeing method according to an exemplary embodiment of the present disclosure includes a seventh step S7 in which, when water is heated in the sixth step S6, a chemical and a dye are injected into the heated water.

The seventh step S7 may further include a step 7-1 in which the required chemical is measured and prepared, a step 7-2 in which, when the temperature of the water reaches 60° C., the chemical is injected into the water, and a step 7-3 in which the dye, which was calculated, is measured and sufficiently dissolved in water and then injected into the water which was injected into the dyeing apparatus.

A hair dyeing method according to an exemplary embodiment of the present disclosure includes an eighth step S8 in which the specific unit of hair is introduced into the dyeing apparatus to be mixed with the water which was injected into the dyeing apparatus.

Here, it is good to stir the water so that the chemical and dye which were injected into the dyeing apparatus and dissolved in the water which was injected into the dyeing apparatus may be well mixed, and so that the dyeing of the specific unit of hair becomes uniform.

A hair dyeing method according to an exemplary embodiment of the present disclosure includes a ninth step S9 in which the temperature of the water is gradually raised up to 100° C.

A hair dyeing method according to an exemplary embodiment of the present disclosure includes a tenth step S10 in which, when the temperature of the water has been raised up to a certain temperature (100° C.), the temperature is maintained for a certain duration of time so that the dye may be sufficiently adhered to the specific unit of hair.

A hair dyeing method according to an exemplary embodiment of the present disclosure includes an eleventh step S11 in which, when a coloring color of the specific unit of hair has been verified as not being a designated required color, the method is repeated starting from the seventh step S7 until the required color is obtained.

If the color of the specific unit of hair is the designated required color, a twelfth step S12 is included in which heating of the water is stopped and the water is drained from the dyeing apparatus.

Here, it is desirable to use a mesh to collect and recycle the hair 1 which is discharged along with the water which is drained from the dyeing apparatus.

A hair dyeing method according to an exemplary embodiment of the present disclosure may further include a thirteenth step S13 in which the specific unit of hair for which dyeing was completed is washed with water.

A fourteenth step S14 may be further included in which the specific unit of hair which was washed with water is softened by dissolving a softening agent in 50° C. water.

A fifteenth step S15 may also be further included in which the specific unit of hair which was softened is dried.

Figure 2:
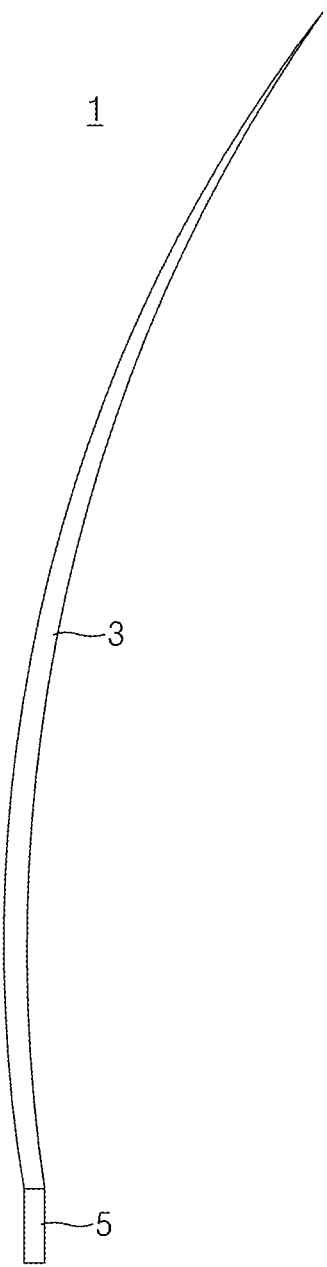
FIG. 2 is a schematic view in which hair which is manufactured by a hair dyeing method according to an embodiment of the present disclosure is illustrated schematically.
Figure 3:
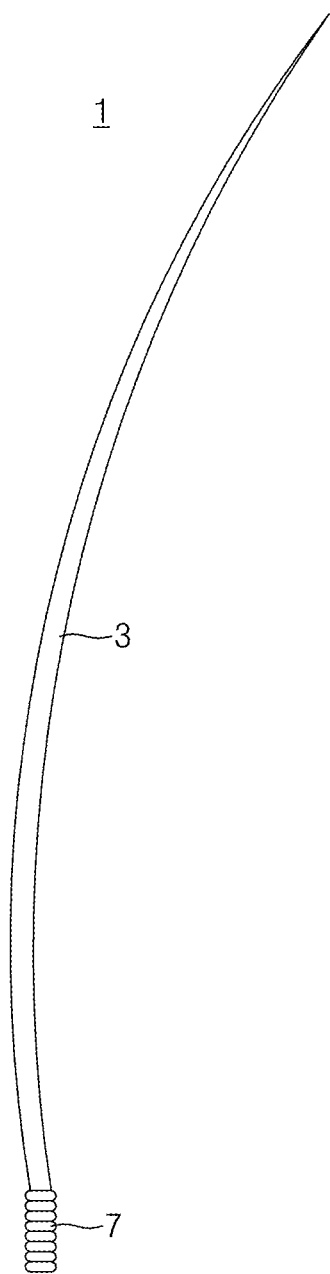
FIG. 3 is a schematic view in which a knotting material which is tied with the hair of FIG. 2 is illustrated schematically.

FIG. 2 is a schematic view in which hair which is manufactured by a hair dyeing method according to an embodiment to an embodiment of the present disclosure is illustrated schematically, and FIG. 3 is a schematic view in which a knotting material which is tied with the hair of FIG. 2 is illustrated schematically.

As illustrated in FIGS. 2 to 3, a hair 1 which is manufactured according to an embodiment of the present disclosure includes a colored part 3 which is colored by a chemical and dye, and an uncolored part 5 which is not colored by the chemical and dye.

A knotting material 7 which is tied to cover the uncolored part 5 so that coloring of the uncolored part 5 during a process of coloring the hair is prevented may be further included to form the uncolored part 5 on the hair 1.

According to the above disclosure, there is an advantage of only root dyeing desired parts with a color which is similar to the scalp by not coloring particular parts of the hair, there is an effect which allows partial dyeing of hair through a process which is simple when compared to related art, and there is an advantage that the method may be applied to human hair and special synthetic hair (polyester).

According to the above disclosure, there is an advantage of only root dyeing on desired parts with a color which is similar to the scalp by excluding coloring on particular parts of the hair.

According to the above disclosure, there is an effect which allows partial dyeing of hair through a process which is simple when compared to related art.

According to the above disclosure, there is an advantage that a partial hair dyeing method may be applied to human hair and special synthetic hair (polyester).

As is disclosed above, although the present disclosure was described with reference to preferred embodiments, it is to be understood that a person with ordinary skill in the art will be able to make various revisions or modifications to the present disclosure without departing from the concept or scope of the present invention as set forth in the following claims.

What is claimed is:

1. A hair dyeing method, comprising steps of:
   (a) applying a first dye to a plurality of hairs;
   (b) dividing the plurality of hairs, to which the first dye is applied, into specific units of hair;
   (c) marking a section in the specific unit of hair which will not be dyed;
   (d) tying the marked section in the specific unit of hair;
   (e) injecting water into a dyeing apparatus which is to be used in applying a second dye;
   (f) heating the water which is injected into the dyeing apparatus;
   (g) injecting a chemical and a dye into the water which is injected into the dyeing apparatus and heated;
   (h) introducing the specific unit of hair to be mixed with the water which is injected into the dyeing apparatus;
   (i) gradually raising a temperature of the water which is injected into the dyeing apparatus;
   (j) when the temperature of the water which is injected into the dyeing apparatus rises to a certain temperature, maintaining the temperature of the water for a certain duration of time;
   (k) verifying the color of the specific unit of hair, and repeating the step (g) when the color of the specific unit of hair is not a designated color; and
   (l) when the color of the specific unit of hair is the designated color, stopping the heating of the water which is injected into the dyeing apparatus, and draining the water from the dyeing apparatus.

2. The method according to claim 1, wherein, in the step (b), the plurality of hairs are divided into the unit of about 2 to about 3 grams.

3. The method according to claim 1, wherein, in the step (f), a steam unit which is installed in the dyeing apparatus is used to heat the water.

4. The method according to claim 1, wherein the step (g) further includes the steps of:
   (g)-1 measuring and preparing the chemical;
   (g)-2 when the water temperature of the water which is injected into the dyeing apparatus reaches 60.degree. C., injecting the chemical into the water which is injected into the dyeing apparatus; and
   (g)-3 measuring and dissolving the calculated dye in water, and then injecting the dye into the water which is injected into the dyeing apparatus.

5. The method according to claim 1, wherein, in the step (h), the water which is injected into the dyeing apparatus is stirred such that the specific unit of hair and the water which is injected into the dyeing apparatus are mixed.

6. The method according to claim 1, wherein, in the step (i), the temperature of the water which is injected into the dyeing apparatus is raised up to about 100° C.

7. The method according to claim 1, wherein, in the step (l), a mesh is used to collect hair which is discharged along with the water which is drained from the dyeing apparatus.

8. The method according to claim 1, further comprising the step of: (m) washing with water the specific unit of hair for which dyeing is completed.

9. The method according to claim 8, further comprising the step of: (n) dissolving a softening agent in 50.degree. C. water to soften the specific unit of hair which is washed with water.

10. The method according to claim 9, further comprising the step of: (o) drying the specific unit of hair which is softened.

11. The method according to claim 1, wherein, in the step (c), the section in the specific unit of hair which will not be dyed is marked by tying a thread thereto.

* * * * *